(12) United States Patent
Govari

(10) Patent No.: US 7,295,877 B2
(45) Date of Patent: Nov. 13, 2007

(54) ENCAPSULATED SENSOR WITH EXTERNAL ANTENNA

(75) Inventor: Assaf Govari, Haifa (IL)

(73) Assignee: Biosense Webster, Inc., Diamond Bar, CA (US)

(*) Notice: Subject to any disclaimer, the term of this patent is extended or adjusted under 35 U.S.C. 154(b) by 485 days.

(21) Appl. No.: 10/632,147

(22) Filed: Jul. 31, 2003

(65) Prior Publication Data

US 2005/0027330 A1 Feb. 3, 2005

(51) Int. Cl.
*A61N 1/00* (2006.01)
(52) U.S. Cl. .................................................. 607/60
(58) Field of Classification Search .............. 607/60, 607/17; 606/102; 623/16.11, 20.2, 20.32
See application file for complete search history.

(56) References Cited

U.S. PATENT DOCUMENTS

| | | | |
|---|---|---|---|
| 4,494,950 A | | 1/1985 | Fischell |
| 4,846,195 A | * | 7/1989 | Alt .............................. 600/595 |
| 5,391,199 A | | 2/1995 | Ben-Haim |
| 5,443,489 A | | 8/1995 | Ben-Haim |
| 5,604,531 A | | 2/1997 | Iddan et al. |
| 5,861,019 A | * | 1/1999 | Sun et al. ...................... 607/60 |
| 6,009,350 A | | 12/1999 | Renken |
| 6,044,297 A | * | 3/2000 | Sheldon et al. ................ 607/17 |
| 6,053,873 A | | 4/2000 | Govari et al. |
| 6,239,724 B1 | | 5/2001 | Doron et al. |
| 6,447,448 B1 | * | 9/2002 | Ishikawa et al. ............. 600/300 |
| 6,484,118 B1 | | 11/2002 | Govari |
| 6,582,365 B1 | | 6/2003 | Hines et al. |
| 2002/0045921 A1 | | 4/2002 | Wolinsky et al. |
| 2002/0065455 A1 | * | 5/2002 | Ben-Haim et al. ........... 600/407 |
| 2002/0095195 A1 | * | 7/2002 | Mass et al. .................... 607/60 |
| 2006/0009856 A1 | * | 1/2006 | Sherman et al. .......... 623/20.32 |

FOREIGN PATENT DOCUMENTS

EP 1 216 654 A2 6/2002
WO WO96/05768 2/1996

OTHER PUBLICATIONS

U.S. Appl. No. 10/029,473, Biosense, Inc.
U.S. Appl. No. 10/029,595, Biosense, Inc.
U.S. Appl. No. 10/173,197, Biosense Inc.
Partial European Search Report EP04254580 dated Oct. 12, 2004.

* cited by examiner

*Primary Examiner*—George Manuel
(74) *Attorney, Agent, or Firm*—Louis J. Capezzuto

(57) ABSTRACT

A medical device, for use inside a body of a mammalian subject, includes a casing adapted for insertion into the body of the mammalian subject, the casing having an outer surface and including an insulating material and an electrically-conductive material, which are arranged so that an area of the outer surface of the casing is electrically conductive. A transmitter is adapted to generate an electrical signal and is encapsulated in the casing and coupled to the conductive material so that the electrically-conductive area of the outer surface serves as an antenna for transmitting the signal to a receiver outside the body.

22 Claims, 5 Drawing Sheets

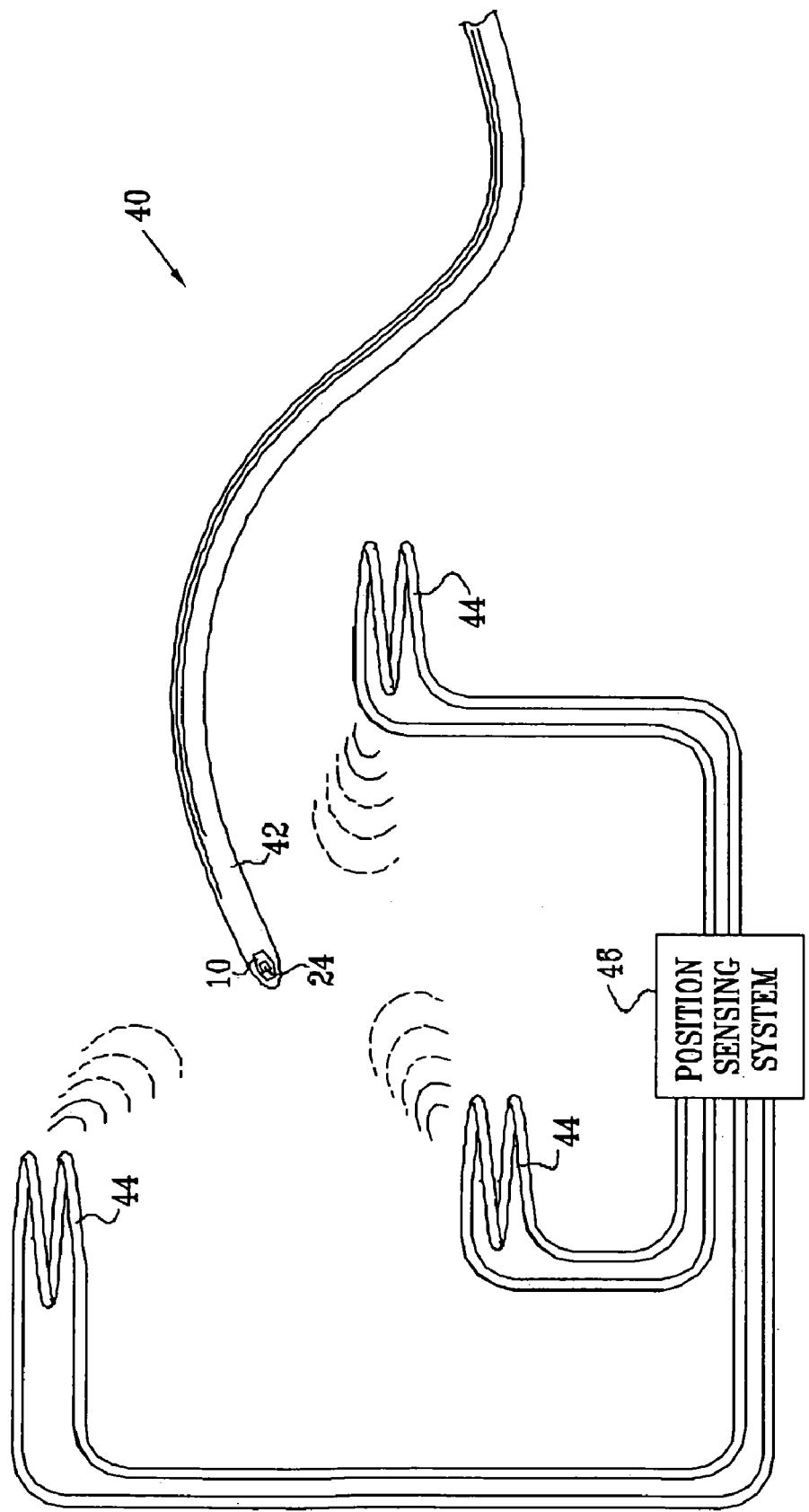

ENCAPSULATED SENSOR WITH EXTERNAL ANTENNA

FIELD OF THE INVENTION

The present invention relates generally to electronic medical devices, and specifically to wireless transmission of radio signals to and from such devices within the body of a patient.

BACKGROUND OF THE INVENTION

The use of encapsulated, wireless sensors within a patient's body is known in the art. Typically, such sensors include a sensing circuit, for detecting a parameter of interest, and a transmitter, with a suitable antenna, for transmitting readings of the parameter to a receiver outside the body. In some applications, the sensor may also be capable of receiving signals and/or radiated power transmitted from outside the body. The parameter detected by the sensing circuit may be a physiological parameter, such as a local pressure, temperature or chemical characteristic (such as pH), or it may be a position parameter, indicative of the position coordinates of the sensor. Generally, all the elements of the sensor are encapsulated in a sealed casing (also referred to as a package or "can") made of a suitable biocompatible material, such as a ceramic or plastic material.

An exemplary wireless position sensor of this sort is described in U.S. Pat. No. 6,239,724, to Doron et al., whose disclosure is incorporated herein by reference. This patent describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

The strength of the signals transmitted by a wireless sensor depends, inter alia, on the size of the antenna that is used to transmit the signals. The ability of the sensor to receive signals is likewise a function of the size of the antenna. Unfortunately, the area of the antenna is limited by the available volume within the sensor casing. For implantable devices, in particular, this volume is very small, and the transmission range of the device may be very short as a result. In response to this problem, U.S. Pat. No. 6,009,350, to Renken, whose disclosure is incorporated herein by reference, suggests using multiple antennas connected in parallel with each other. The antennas may be mounted within the can of the implantable device or externally.

As another example, U.S. Pat. No. 6,053,873, to Govari et al., whose disclosure is incorporated herein by reference, describes a stent having a sensor for measuring characteristics of a fluid flow passing through the stent and a transmitter for transmitting flow parameters to a receiver outside the body. The stent comprises a coil, which also serves as an antenna, for receiving energy from an electromagnetic field irradiating the body so as to power the transmitter. In one embodiment, the transmitter is based on a tunnel diode oscillator circuit, suitably biased so as to operate in a negative resistance regime.

SUMMARY OF THE INVENTION

Embodiments of the present invention provide techniques for improving the coupling between a wireless device inside the body and a transmitter or receiver outside the body, by using a portion of the casing of the device as an antenna. The casing, which is typically sealed, comprises a conductive external area, which is coupled to circuitry inside the casing so as to serve as all or part of the device antenna. Using the outer surface of the casing as an antenna in this fashion increases the active area of the antenna, without necessarily increasing the overall size of the device.

In some embodiments of the present invention, the conductive external area of the casing is designed to contact conductive structures outside the device casing. For example, when the device is used in conjunction with a metal implant, the conductive area may contact the implant, in such a way that a part or all of the implant serves as the device antenna. Alternatively or additionally, when the casing of the device is in contact with conductive body fluids, such as blood or other electrolytes, ionic currents in the fluids may be used to enhance the antenna signals transmitted and received through the conductive area of the casing.

The principles of the present invention are applicable particularly to implantable devices, but may also be applied to invasive tools, such as catheters. Typically (although not necessarily), the wireless device comprises a sensor, which is coupled to communicate via the conductive area of the casing with a receiver outside the body. The sensor may comprise a position sensor, which generates signals for transmission to the receiver that are indicative of the position and/or orientation coordinates of the device. Alternatively or additionally, the sensor may comprise a transducer for detecting physiological parameters, such as temperature, pressure, chemical properties, or substantially any other type of parameter that is amenable to sensing by such a device.

There is therefore provided, in accordance with an embodiment of the present invention, a medical device for use inside a body of a mammalian subject, the device including:

a casing adapted for insertion into the body of the mammalian subject, the casing having an outer surface and including an insulating material and an electrically-conductive material, which are arranged so that an area of the outer surface of the casing is electrically conductive; and a transmitter, which is adapted to generate an electrical signal and is encapsulated in the casing and coupled to the conductive material so that the electrically-conductive area of the outer surface serves as an antenna for transmitting the signal to a receiver outside the body.

Typically, the insulating material includes at least one of a ceramic material and a plastic material.

In one embodiment, the casing has an inner surface, and wherein the electrically-conductive material is arranged to fill an entire thickness of the casing between the inner surface and the electrically-conductive area of the outer surface. In another embodiment, the conductive material is arranged in a layer overlying the insulating material in the electrically-conductive area.

In one embodiment, the electrically-conductive area is configured to contact a metal implant within the body of the mammalian subject while transmitting the signal.

In another embodiment, the electrically-conductive area is configured to contact an electrically-conductive body fluid while transmitting the signal. Typically, the electrically-conductive area is configured to contact the electrically-conductive body fluid in at least one of a digestive tract and a vascular system of the body.

In some embodiments, the device includes a sensor, which is encapsulated within the casing and is adapted to sense a parameter associated with a location of the device within the body, wherein the sensor is coupled to the transmitter so that the signal generated by the transmitter is indicative of the sensed parameter. In one of these embodiments, the sensor includes a position sensor, such that the signal generated by the transmitter is indicative of a position coordinate of the device. In other embodiments, the parameter includes a physiological parameter, and the sensor may include at least one of a pressure sensor, a temperature sensor, a flow sensor, a chemical sensor, an electrical sensor and an optical sensor.

There is also provided, in accordance with an embodiment of the present invention, a medical implant, including:

an implantable member, including a metallic material, which is adapted to be implanted in a body of a mammalian subject; and a signal transmission device, including:

a casing having an outer surface and including an insulating material and an electrically-conductive material, which are arranged so that an area of the outer surface of the casing, in contact with the metallic material of the implantable member, is electrically conductive; and a transmitter, which is adapted to generate an electrical signal and is encapsulated in the casing and coupled to the conductive material so that the electrically-conductive area of the outer surface serves as an antenna for transmitting the signal to a receiver outside the body.

In one embodiment, the implantable member includes an implantable orthopedic device.

There is additionally included, in accordance with an embodiment of the present invention, an invasive medical tool, including:

an insertion member, having a distal end, which is adapted to be inserted into a body of a mammalian subject; and a signal transmission device, contained within the distal end of the insertion member and including:

a casing having an outer surface and including an insulating material and an electrically-conductive material, which are arranged so that an area of the outer surface of the casing is electrically conductive;

a sensor, which is encapsulated within the casing and is adapted to sense a parameter associated with a location of the distal end of the insertion member within the body; and a transmitter, which is adapted to generate an electrical signal that is indicative of the parameter sensed by the sensor, and which is encapsulated in the casing and coupled to the conductive material so that the electrically-conductive area of the outer surface serves as an antenna for transmitting the signal to a receiver outside the body.

In one embodiment, the sensor includes a position sensor, such that the electrical signal generated by the transmitter is indicative of a position coordinate of the device, and the tool includes a receiver, which is adapted to receive the electrical signal transmitted by the antenna and to process the electrical signal so as to determine coordinates of the insertion member within the body. The insertion member may include a catheter.

There is further provided, in accordance with an embodiment of the present invention, a position sensing system, including:

a position sensing device, for insertion into a body of a mammalian subject, the device including:

a casing adapted for insertion into the body, the casing having an outer surface and including an insulating material and an electrically-conductive material, which are arranged so that an area of the outer surface of the casing is electrically conductive;

a sensor, which is encapsulated within the casing and is adapted to sense a parameter indicative of a position of the device within the body; and a transmitter, which is adapted to generate an electrical signal that is indicative of the parameter sensed by the sensor, and which is encapsulated in the casing and coupled to the conductive material so that the electrically-conductive area of the outer surface serves as an antenna for transmitting the signal to a receiver outside the body; and a receiver, which is adapted to receive the electrical signal transmitted by the antenna and to process the electrical signal so as to determine coordinates of the device within the body.

There is moreover provided, in accordance with an embodiment of the present invention, a method for transmitting a signal from inside a body of a mammalian subject, the method including:

encapsulating an electronic device including a transmitter in a casing having an outer surface and including an insulating material and an electrically-conductive material, which are arranged so that an area of the outer surface of the casing is electrically conductive;

coupling the transmitter to the conductive material so that the electrically-conductive area of the outer surface serves as an antenna for the transmitter;

inserting the casing containing the device into the body of the mammalian subject; and transmitting the signal from the transmitter within the body via the antenna to a receiver outside the body.

In one embodiment, inserting the casing includes making contact between the electrically-conductive area and a metal implant that is placed within the body of the mammalian subject, so as to increase a gain of the antenna in transmitting the signal. Typically, the metal implant includes an orthopedic implant, and inserting the casing includes fixing the orthopedic implant to a bone in the body.

In another embodiment, inserting the casing includes bringing the electrically-conductive area into contact with an electrically-conductive body fluid while transmitting the signal, so as to increase a gain of the antenna in transmitting the signal.

In still another embodiment, transmitting the signal includes sensing a parameter associated with a location of the device within the body, wherein the transmitted signal is indicative of the sensed parameter. Typically, the transmitted signal is indicative of a position coordinate of the device, and the method includes receiving and processing the signal outside the body in order to determine the position coordinate.

The present invention will be more fully understood from the following detailed description of the embodiments thereof, taken together with the drawings in which:

BRIEF DESCRIPTION OF THE DRAWINGS

FIG. 3 is a schematic side view of a system for detecting position coordinates of a catheter, in accordance with an embodiment of the present invention;

DETAILED DESCRIPTION OF EMBODIMENTS

Figure 1A:
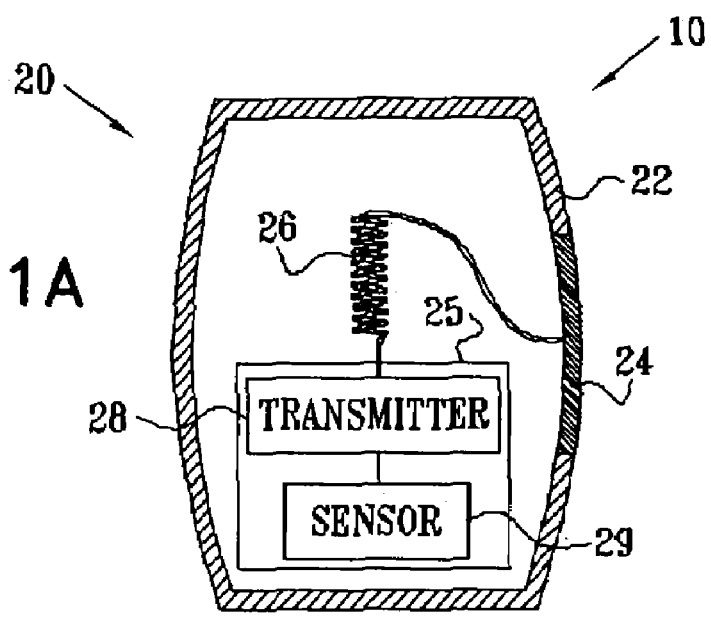
FIG. 1A is a schematic, sectional illustration of a wireless device for use inside the body of a subject, in accordance with an embodiment of the present invention.
Figure 1B:
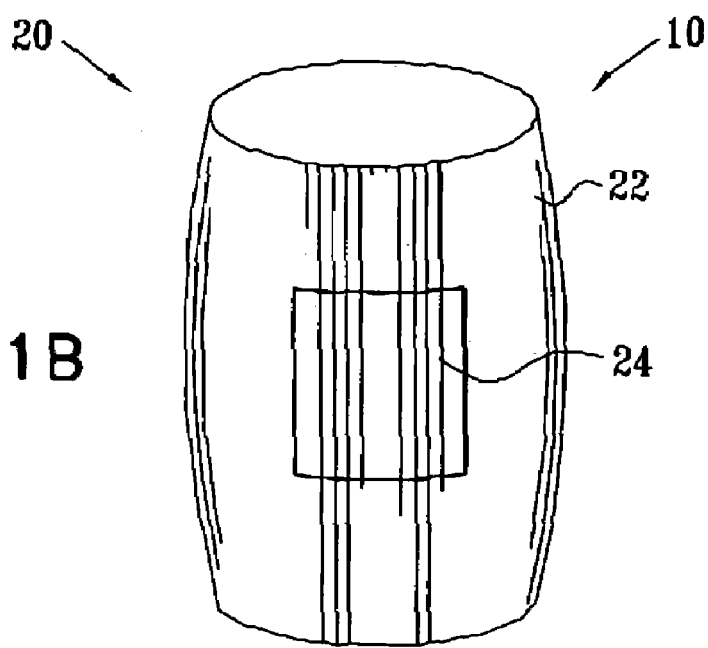
FIG. 1B is a schematic, pictorial illustration of the device of FIG. 1A.

Reference is now made to FIGS. 1A and 1B, which schematically illustrate a wireless device 10 for use inside the body of a mammalian subject, in accordance with an embodiment of the present invention. FIG. 1A is a sectional view of the device, while FIG. 1B is a pictorial illustration of the device exterior. Device 10 comprises circuitry that is contained within a sealed casing 20. The casing comprises an insulating material 22, such as a ceramic or plastic material, with a conductive area 24, typically made of a suitable biocompatible metal. In this embodiment, the entire thickness of the casing in area 24 is metal, which is fastened and sealed to the surrounding insulating material 22 by a suitable metal/ceramic or metal/plastic seal, as is known in the art.

Device 10 comprises electrical circuitry 25, which is encapsulated inside casing 20. The circuitry typically comprises a transmitter 28, which is coupled to transmit signals via conductive area 24 to one or more receivers outside the patient's body (not shown in this figure). Area 24 thus serves as the antenna for the transmitter, either by itself or in conjunction with an internal antenna 26 inside casing, 20. The internal antenna, if used, may be coupled to area 24 either in series, as shown in FIG. 1A, or in parallel. Area 24 may also be electrically coupled to conductive structures outside device 10, for enhancing the antenna gain, as described further hereinbelow.

Typically, circuitry 25 further comprises a sensor 29, which generates signals that are transmitted by transmitter 28. In some embodiments of the present invention, sensor 29 comprises a position sensor, which generates a position signal indicative of the coordinates of device 10 inside the patient's body. The sensor may comprise a wireless electromagnetic position sensor, as described, for example, in the above-mentioned U.S. Pat. No. 6,239,724, or as described in U.S. Patent Application 10/029,473. Alternatively, the sensor may generate the position signal in response to ultrasonic beams directed toward device 10, as described, for example, in U.S. Patent Application 10/029,595. Both of these patent applications are assigned to the assignee of the present patent application, and their disclosures are incorporated herein by reference. The use and characteristics of position sensors in device 10 are described in further detail hereinbelow with reference to FIG. 3.

Alternatively or additionally, sensor 29 may be configured to sense a physiological parameter in the vicinity of device 10 within the body. For this purpose, it may be necessary for the sensor to be in contact with casing 20 and possibly to protrude through the casing. For example, sensor 29 may comprise a pressure sensor, such as a piezoelectric pressure transducer; a flow sensor, based on an ultrasound transducer or bioimpedance measurement element; a chemical sensor, such as a pH sensor or oxygen saturation sensor; a temperature sensor; an electrical activity sensor; an optical or imaging sensor; or substantially any other type of miniaturized sensing device known in the art. Some sensors of these types are described in the above-mentioned U.S. Pat. No. 6,053,873.

Circuitry 25 typically comprises other elements known in the art, which are not shown in the figures for the sake of simplicity. For example, circuitry 25 generally comprises means for providing power to transmitter 28, such as a battery or a receiver circuit, for receiving energy radiated toward device 20 from an external source (not shown). Devices adapted for this sort of battery-less operation are described in the above-mentioned U.S. Pat. Nos. 6,053,873 and 6,239,724 and in U.S. Patent Application 10/029,473. Circuitry 25 may also comprise a receiver, which is coupled to receive interrogation signals from a transmitter outside the body (not shown), and to prompt transmitter 28 to send a response. Other components that may be included in circuitry 25 will be apparent to those skilled in the art.

Figure 2A:
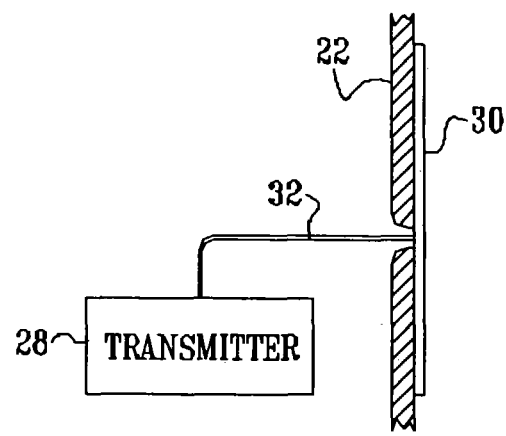
FIG. 2A is a schematic, detail illustration showing coupling between a sensor and an antenna in a wireless device for use inside the body of a subject, in accordance with an embodiment of the present invention.

FIG. 2A is a schematic detail illustration showing a conductive area 30 on the casing of a wireless device for use inside the body, in accordance with another embodiment of the present invention. In this embodiment, conductive area 30 typically comprises a conductive, non-ferromagnetic coating formed over the outer surface of non-conducting material 22 that makes up the casing. Transmitter 28 is connected to area 30 by a feed-through 32, passing through material 22. This arrangement of area 30 is advantageous in that it may simplify the production of the casing, as well as allowing area 30 to take on a greater variety of different shapes.

Figure 2B:
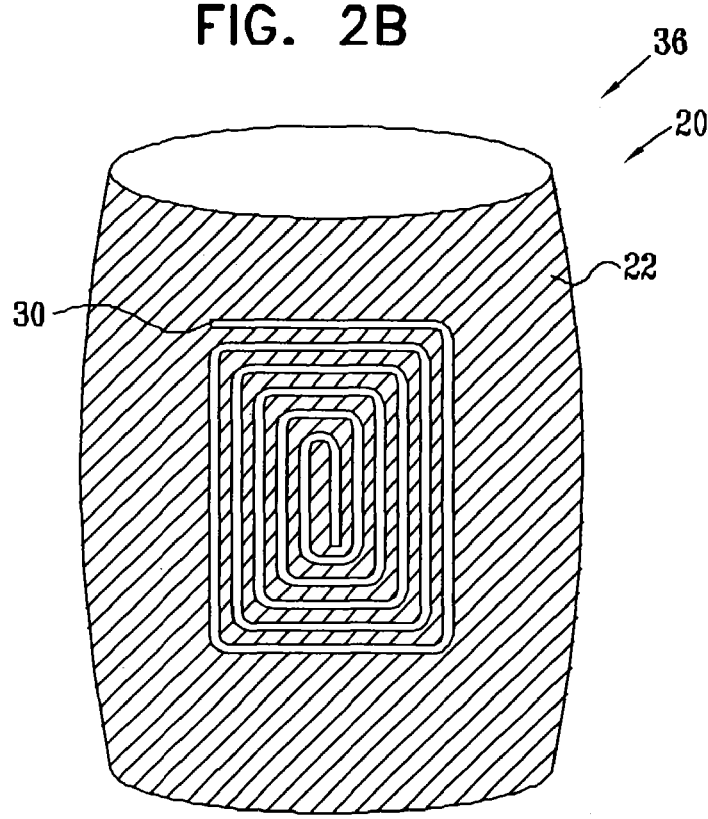
FIG. 2B is a schematic, pictorial illustration showing a coil antenna formed on a casing of a wireless device for use inside the body of a subject, in accordance with an embodiment of the present invention.

FIG. 2B is a schematic, pictorial illustration of another wireless device 36 for use inside the body of a subject, in accordance with an alternative embodiment of the present invention. In this embodiment, area 30 is formed over material 22 on the outer surface of casing 20, as shown in FIG. 2A, so as to define a conducting spiral. The characteristics of the spiral (as well as of the other types of antennas described herein) are typically optimized for a particular transmission frequency, such as in the 433 MHz band or in the 800-900 MHz band, depending on application requirements. Feed-throughs connect the ends of the spiral to the transmitter inside the casing. Alternatively, area 30 may be formed in substantially any shape that is useful as an antenna, and may in some cases cover substantially the entire exterior of casing 20, as long as there is no additional antenna inside the casing that must be able to transmit or receive signals through the casing. Although applications of the present invention are described hereinbelow with reference to device 10, as shown in FIGS. 1A and 1B, it will be understood that devices with conductive areas of other shapes and forms, such as device 36, may likewise be used in these applications.

FIG. 3 is a schematic side view of a system 40 for guiding a catheter 42 inside the body of a patient, in accordance with an embodiment of the present invention. Device 10 is contained within a distal end of catheter 42, which is inserted into the patient's body, typically through the vascular or digestive system. A set of reference coils 44 are fixed in known positions outside the body, and receive position signals generated by device 10. A position sensing system 46 analyzes the signals in order to determine position and, optionally, orientation coordinates of device 10 (and thus of catheter 42) within the body. Methods for determining coordinates of a position sensor inside the body in the configuration of system 40 are known in the art, as described, for example, in U.S. Pat. Nos. 5,391,199 and 5,443,489, to Ben-Haim, whose disclosures are incorporated herein by reference. The use of device 10 in such a system is advantageous, however, in that it requires no wires to carry the position signals generated by device 10 between the distal and proximal ends of catheter 42. Although the exemplary embodiment of FIG. 3 illustrates the use of device 10 in a catheter, the device may be used in like fashion in different sorts of invasive medical instruments, as will be apparent to those skilled in the art.

In another embodiment of the present invention, sensor 29 in device 10 (shown in FIG. 1) is configured as an AC magnetic field receiver, which senses an AC magnetic field generated by a plurality of magnetic field transmitters outside the body of the patient. Coils 44, for example, may be configured to serve as the magnetic field transmitters. These transmitters are also referred to as magnetic field generators or radiators, and generate respective AC magnetic fields to define a fixed frame of reference. Position sensors of this type are further described in PCT application PCT/US95/01103, published as WO96/05768 (U.S. patent application Ser. No. 08/293,859 filed Aug. 19, 1994), whose disclosure is incorporated herein by reference.

The position and orientation coordinates of device 10 within the body are ascertained by determining the position and orientation coordinates of the position sensor. Typically, the position sensor comprises one or more antennas, for example one or more coils, which are irradiated by two or three radiators (transmitters) outside the body surface of the patient.

The transmitters may be arranged in any convenient position and orientation, so long as they are fixed in respect to some reference frame, and so long as the transmitters are non-overlapping, that is, there are no two transmitters with the exact, identical location, i.e. position and orientation. When driven by a suitable radiator driver (not shown), the transmitters generate a multiplicity of distinguishable AC magnetic fields that form the magnetic field sensed by receiving antennas in the position sensor. The magnetic fields are distinguishable with regard to the frequency, phase, or both frequency and phase of the signals in the respective magnetic fields. Time multiplexing is also possible.

Placement of the transmitters, as well as their size and shape, will vary according to the application of the invention. In one embodiment, useful in a medical application, the transmitters comprise wound annular coils from about 2 to 20 cm in outer diameter (O.D.) and from about 0.5 to 2 cm thick, in a coplanar, triangular arrangement, wherein the centers of the coils are from about 2 to 30 cm apart. Bar-shaped transmitters or even triangular or square-shaped coils could also be useful for such medical applications. In instances in which a prone patient is the subject of a procedure involving the instant invention, the transmitters are preferably positioned in or below the surface upon which the patient is resting (such as an operating table), below the portion of the patient's body upon which the procedure is being performed. In other applications, the transmitters may be close to the skin of the patient. The transmitters are driven by a radiator driver, preferably in a manner described below.

The position sensor in device 10 may consist of a single coil, or may alternatively include two or more sensor coils wound on either air cores or a core of material (not shown). In one embodiment, the coils have mutually orthogonal axes, in known alignment relative to the geometry of device 10. Unlike prior art position sensors (used for other applications), which contain three coils that are concentrically located, or at least whose axes intercept, the coils used in sensor 29 may be closely spaced along a longitudinal axis, in order to reduce the diameter of the sensor and thus reduce the size of device 10.

The signals received by the receiving antennas (coils) of the position sensor in device 10 are processed and transmitted by transmitter 28 to a receiver associated with position sensing system 46, outside the patient's body. System 46 also receives a representation of the signals used to drive the transmitters. System 46 processes the signals to provide a display or other indication of the position and orientation of device 10 within the body, typically on a monitor or other display.

To measure the six-dimensional position and orientation of device 10 (X, Y, Z directions and pitch, yaw and roll orientations) in a fixed frame of reference requires at least two-non-overlapping transmitters outside the body, which generate at least two distinguishable AC magnetic fields; and at least two non-parallel coils in sensor 29 to measure the magnetic field flux resulting from the magnetic fields. In some embodiments, three coils are used in sensor 29 to improve the accuracy and reliability of the position measurement. In other applications in which fewer dimensions are required, only a single coil may be necessary for the position sensor. In this case, the position sensing system determines five position and orientation coordinates of device 10 (X, Y, Z directions and pitch and yaw orientations). Specific features and functions of a single coil system (also referred to as a single axis system) are described in U.S. Pat. No. 6,484,118, whose disclosure is incorporated herein by reference.

In one embodiment of the invention, the coils used in sensor 29 have an inner diameter of 0.5 mm and have 800 turns of 16 micrometer diameter to give an overall coil diameter of 1-1.2 mm. The effective capture area of the coils is typically about 400 mm$^2$. It will be understood that these dimensions may vary over a considerable range and are only representative of a particular range of dimensions. In particular, the size of the coils can be as small as 0.3 mm (with some loss of sensitivity) and as large as 2 or more mm. The wire size of the coils can range from 10-31 μm and the number of turns between 300 and 2600, shaped depending on the maximum allowable size and the wire diameter. The effective capture area should be made as large as feasible, consistent with the overall size requirements of device 10. Although the preferred sensor coil shape is cylindrical, other shapes can also be used. For example, a barrel shaped coil or square or other shaped coils may be useful depending on the geometry of device 10.

Wireless position sensor devices in accordance with the principles of the present invention may also be implanted in the body (temporarily or permanently). For example, a device of this sort may be used in a wireless tag, which is implanted in a patient's body to mark the location of a planned diagnostic or therapeutic procedure. The use of wireless tags for this purpose is described in U.S. patent application Ser. No. 10/173,197 filed on Jun. 17, 2002, whose disclosure is incorporated herein by reference.

Figure 4A:
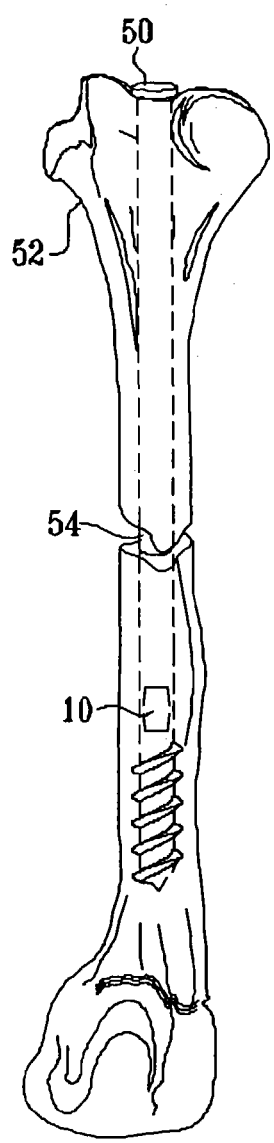
FIG. 4A is a schematic, cutaway view of a nail implanted inside a bone, with a wireless device connected to the nail, in accordance with an embodiment of the present invention.
Figure 4B:
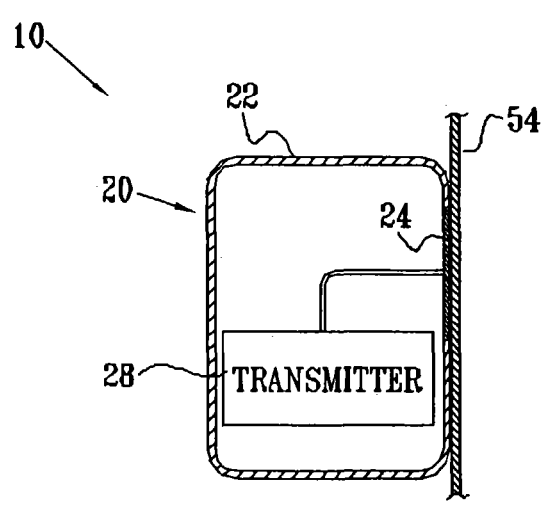
FIG. 4B is a schematic, sectional view of the device of FIG. 4A and a portion of the nail in contact with the device.

Reference is now made to FIGS. 4A and 4B, which schematically illustrate the use of device 10 in conjunction with an intramedullary nail 50, in accordance with another embodiment of the present invention. FIG. 4A is a schematic, cutaway view of a broken bone 52, into which nail 50 has been inserted, as is known in the art. FIG. 4B is a sectional view of device 10, which shows details of the relation of the device to a metal outer surface 54 of nail 50. Conductive area 24 of device casing 20 is electrically coupled to surface 54, so that in effect, nail 50 serves as a giant antenna for transmitter 28. Typically, device 10 is simply fastened in place so that area 24 makes a conductive contact with surface 54. Alternatively, an inductive or capacitive coupling scheme may be used.

Figure 5:
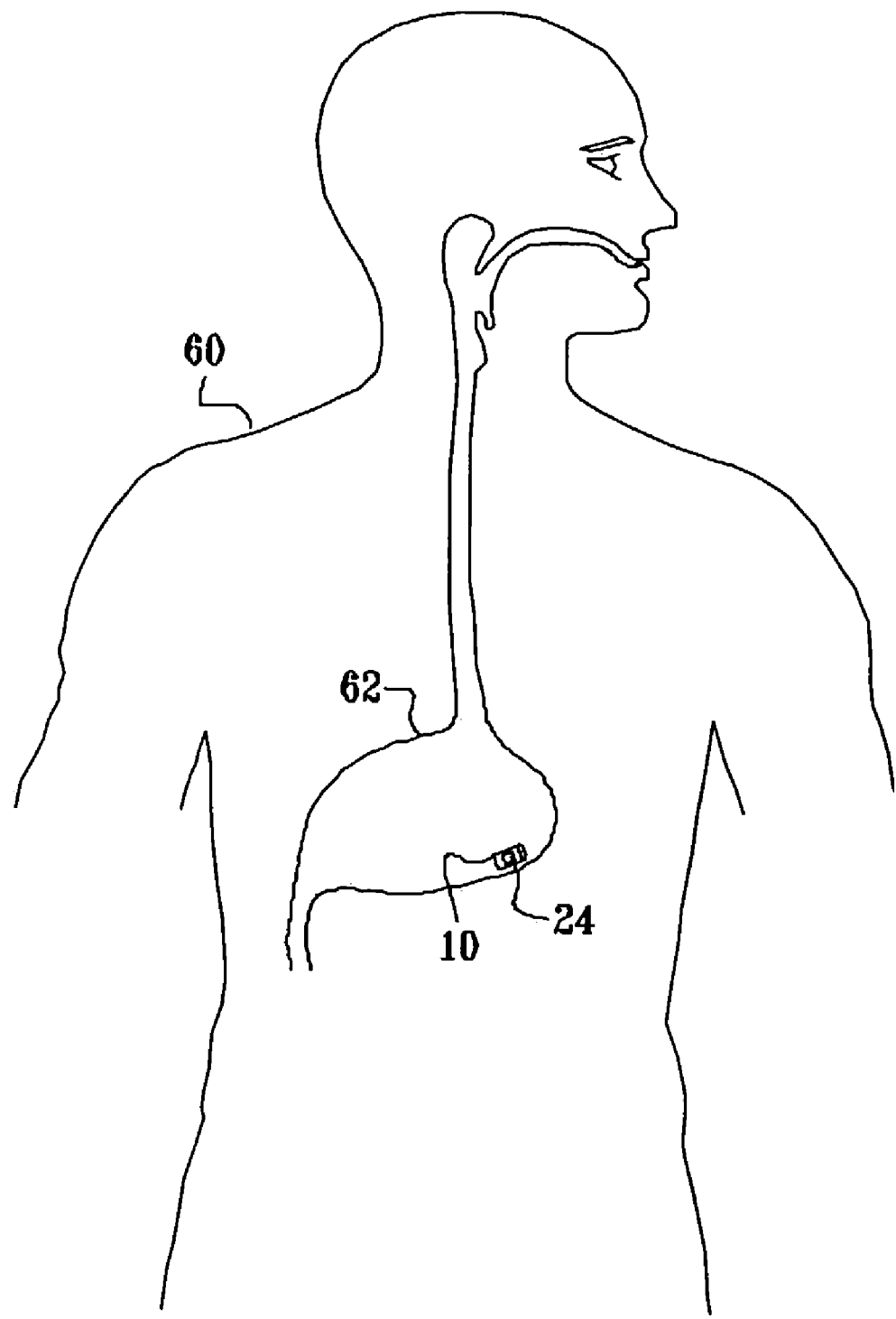
FIG. 5 is a schematic, cutaway view of the digestive tract of a subject, showing a wireless device inside the subject's stomach, in accordance with an embodiment of the present invention.

FIG. 5 is a schematic cutaway view of a digestive tract 62 of a patient 60, showing the use of device 10 in this context, in accordance with still another embodiment of the present invention. In this embodiment, device 10 has the form of a pill, which is swallowed by patient 60. As the pill passes through digestive tract 62, it senses local characteristics and uses conductive area 24 to transmit signals to receivers outside the body (not shown in this figure). For example, device 10 may sense temperature, pressure or acidity of the digestive fluids. Alternatively or additionally, device 10 may comprise a miniature electronic image sensor, with suitable optics, which captures and transmits images of the digestive tract. This sort of "video pill" is described, for example, in U.S. Pat. No. 5,604,531, whose disclosure is incorporated herein by reference.

Conductive area 24 on device 10 makes electrical contact with the digestive fluids in which the device is immersed, and/or with the walls of the digestive tract. To the extent that these fluids are electrolytic, the signals transmitted by device 10 through area 24 cause an ionic current to flow in the fluids. The ionic current causes electromagnetic radiation at the signal frequencies, so that in effect, a portion of digestive tract 62 acts as an extended antenna for device 10. (Thus, the signals received outside the body from device 10 may be stronger, although the effect of the biological "extended antenna" may be unpredictable.) In a similar manner, if area 24 is in contact with blood or lymphatic fluid, a portion of the vascular system or lymphatic system could serve as an extended antenna. Since soft tissues also comprise substantial electrolyte content, these tissues could be exploited in a similar manner to enhance the antenna gain of device 10. In order to improve the electrical contact between area 24 and the body fluids or tissues, the outer surface of area 24 may be roughened, or it may be coated with metal particles, such as titanium.

Although aspects of the present invention are described above with reference to certain particular applications, other applications of the principles of the present invention will be apparent to those skilled in the art. For example, device 10 may be adapted for implantation in the head of a patient for purposes of brain stimulation and/or monitoring. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical device for use inside a body of a mammalian subject, the device comprising:
   a casing adapted for insertion into the body of the mammalian subject, the casing having an outer surface and comprising an insulating material surrounding a conductive area made of an electrically-conductive material, the conductive area fastened and sealed to the insulation material; and
   a transmitter, which is adapted to generate an electrical signal and is encapsulated in the casing and coupled to the conductive area so that the electrically-conductive area of the outer surface serves as an antenna for transmitting the signal to a receiver outside the body, the signal being a position signal indicative of six-dimensional position and orientation including X, Y, Z directions and pitch, yaw and roll orientations.

2. The device according to claim 1, wherein the insulating material comprises at least one of a ceramic material and a plastic material.

3. The device according to claim 1, wherein the casing has an inner surface, and wherein the electrically-conductive material is arranged to fill an entire thickness of the casing between the inner surface and the electrically-conductive area of the outer surface.

4. The device according to claim 1, wherein the conductive material is arranged in a layer overlying the insulating material in the electrically-conductive area.

5. The device according to claim 1, wherein the electrically-conductive area is configured to contact a metal implant within the body of the mammalian subject while transmitting the signal.

6. The device according to claim 1, wherein the electrically-conductive area is configured to contact an electrically-conductive body fluid while transmitting the signal.

7. The device according to claim 6, wherein the electrically-conductive area is configured to contact the electrically-conductive body fluid in at least one of a digestive tract and a vascular system of the body.

8. The device according to claim 1, and comprising a sensor, which is encapsulated within the casing and is adapted to sense a parameter associated with a location of the device within the body, wherein the sensor is coupled to the transmitter so that the signal generated by the transmitter is indicative of the sensed parameter.

9. The device according to claim 8, wherein the sensor comprises a position sensor, such that the signal generated by the transmitter is indicative of a position coordinate of the device.

10. The device according to claim 8, wherein the parameter comprises a physiological parameter.

11. The device according to claim 10, wherein the sensor comprises at least one of a pressure sensor, a temperature sensor, a flow sensor, a chemical sensor, an electrical sensor and an optical sensor.

12. A medical implant, comprising:
   an implantable member, comprising a metallic material, which is adapted to be implanted in a body of a mammalian subject; and
   a signal transmission device, comprising:
   a casing having an outer surface and comprising an insulating material surrounding a conductive area made of an electrically-conductive material, the conductive area fastened and sealed to the insulating material; and
   a transmitter, which is adapted to generate an electrical signal and is encapsulated in the casing and coupled to the conductive area so that the electrically-conductive area of the outer surface serves as an antenna for transmitting the signal to a receiver outside the body, the signal being a position signal indicative of six-dimensional position and orientation including X, Y, Z directions and pitch, yaw and roll orientations.

13. The implant according to claim 12, wherein the implantable member comprises an implantable orthopedic device.

14. A method for transmitting a signal from inside a body of a mammalian subject, the method comprising:
- encapsulating an electronic device comprising a transmitter in a casing having an outer surface and comprising an insulating material surrounding a conductive area made of an electrically-conductive material, the conductive area fastened and sealed to the insulating material;
- coupling the transmitter to the conductive material so that the electrically-conductive area of the outer surface serves as an antenna for the transmitter;
- inserting the casing containing the device into the body of the mammalian subject; and
- transmitting the signal from the transmitter within the body via the antenna to a receiver outside the body, the signal being a position signal indicative of six-dimensional position and orientation including X, Y, Z directions and pitch, yaw and roll orientations.

15. The method according to claim 14, wherein inserting the casing comprises making contact between the electrically-conductive area and a metal implant that is placed within the body of the mammalian subject, so as to increase a gain of the antenna in transmitting the signal.

16. The method according to claim 15, wherein the metal implant comprises an orthopedic implant, and wherein inserting the casing comprises fixing the orthopedic implant to a bone in the body.

17. The method according to claim 14, wherein inserting the casing comprises bringing the electrically-conductive area into contact with an electrically-conductive body fluid while transmitting the signal, so as to increase a gain of the antenna in transmitting the signal.

18. The method according to claim 17, wherein bringing the electrically-conductive area into contact comprises contacting the electrically-conductive body fluid in at least one of a digestive tract and a vascular system of the body.

19. The method according to claim 14, wherein transmitting the signal comprises sensing a parameter associated with a location of the device within the body, wherein the transmitted signal is indicative of the sensed parameter.

20. The method according to claim 19, wherein inserting the casing comprises fixing the casing to an invasive medical tool, and processing the signal comprises determining the location of the tool within the body.

21. The method according to claim 19, wherein sensing the parameter comprises sensing a physiological parameter with respect to the body.

22. The method according to claim 21, wherein sensing the physiological parameter comprises sensing at least one of a pressure, a temperature, a flow characteristic, a chemical characteristic, an electrical characteristic and an optical characteristic.

* * * * *